(12) United States Patent
Kohama et al.

(10) Patent No.: US 6,262,014 B1
(45) Date of Patent: Jul. 17, 2001

(54) 5-BENZYLHEXANOL-2 AND PERFUME COMPOSITION CONTAINING IT

(75) Inventors: Makoto Kohama; Junji Koshino, both of Wakayama; Nao Toi; Kazuyuki Fukuda, both of Tokyo, all of (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/091,819

(22) PCT Filed: Oct. 22, 1996

(86) PCT No.: PCT/JP96/03057

§ 371 Date: Jun. 25, 1998

§ 102(e) Date: Jun. 25, 1998

(87) PCT Pub. No.: WO97/25302

PCT Pub. Date: Jul. 17, 1997

(30) Foreign Application Priority Data

Jan. 10, 1996 (JP) .................................... 8-002148

(51) Int. Cl.[7] .............................. A61K 7/46; C07C 33/34
(52) U.S. Cl. ............................... 512/20; 512/25; 568/715; 568/716
(58) Field of Search ..................... 512/20, 25; 568/716, 568/715

(56) References Cited

U.S. PATENT DOCUMENTS

| | | | | |
|---|---|---|---|---|
| 4,206,090 | * | 6/1980 | Schmitt | 424/64 |
| 4,610,812 | * | 9/1986 | Hall | 512/4 |
| 5,552,380 | * | 9/1996 | Sprecker et al. | 512/20 |

OTHER PUBLICATIONS

"Stereochemistry of the Intramoleulcar Electrophilic Attack of an Aldehyde on a Carbon–Tin Bond." Tetrahedron (1986), 42(12), 3181–98, 1986.*

* cited by examiner

Primary Examiner—Jill Warden
Assistant Examiner—Monique Cole
(74) Attorney, Agent, or Firm—Oblon, Spivak, McClelland, Maier & Neustadt, P.C.

(57) ABSTRACT

The present invention relates to 5-benzylhexanol-2 and a perfume composition comprising the same. The perfume composition according to the present invention has a floral scent, high stability and, in the mixture system of a product, excellent scent lasting property.

8 Claims, 1 Drawing Sheet

5-BENZYLHEXANOL-2 AND PERFUME COMPOSITION CONTAINING IT

TECHNICAL FIELD

The present invention relates to a novel fragrant compound and a perfume composition containing the compound. More specifically, the present invention pertains to 5-benzylhexanol-2 which has a floral scent and excellent lasting property in a mixture system of each of fragrant products such as toiletry products, household products and personal care products.

BACKGROUND ART

A number of perfume materials with a floral scent have conventionally been known. Among them, aroma chemicals with aldehyde moiety, typified by Lilial, are greatest in number and besides, they form an important category. They are however not always stable in fragrant products which have various pHs or various product forms. Accordingly, it is often difficult to impart the products with freshness, natural feeling, mildness, voluminous feeling or stable lasting property and there is a limitation in the perfume preparation.

In addition, many floral aroma chemicals with alcohol moiety have been known and the typical example of them is phenethyl alcohol. Phenethyl alcohol itself is poor in lasting property so that it cannot easily impart perfumery products with a stable lasting scent.

Accordingly, an object of the present invention is to provide a novel compound which has a floral scent, high stability and excellent lasting property in a mixture system; and also a perfume composition comprising the compound.

DISCLOSURE OF THE INVENTION

Under such situations, the present inventors synthesized compounds having various functional groups and investigated their scents and mixture systems. As a result, it has been found that 5-benzylhexanol-2 which is a novel compound represented by the below-described formula has a floral scent, and in the mixture system of a product, has freshness, natural feeling, mildness, voluminous feeling and stable lasting scent, leading to the completion of the present invention.

The present invention therefore provides 5-benzylhexanol-2 represented by the following formula (1):

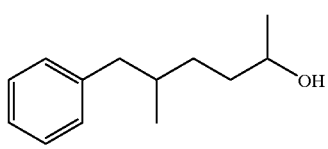

(1)

and a perfume composition comprising the same.

BEST MODE FOR CARRYING OUT THE INVENTION

Figure 1:
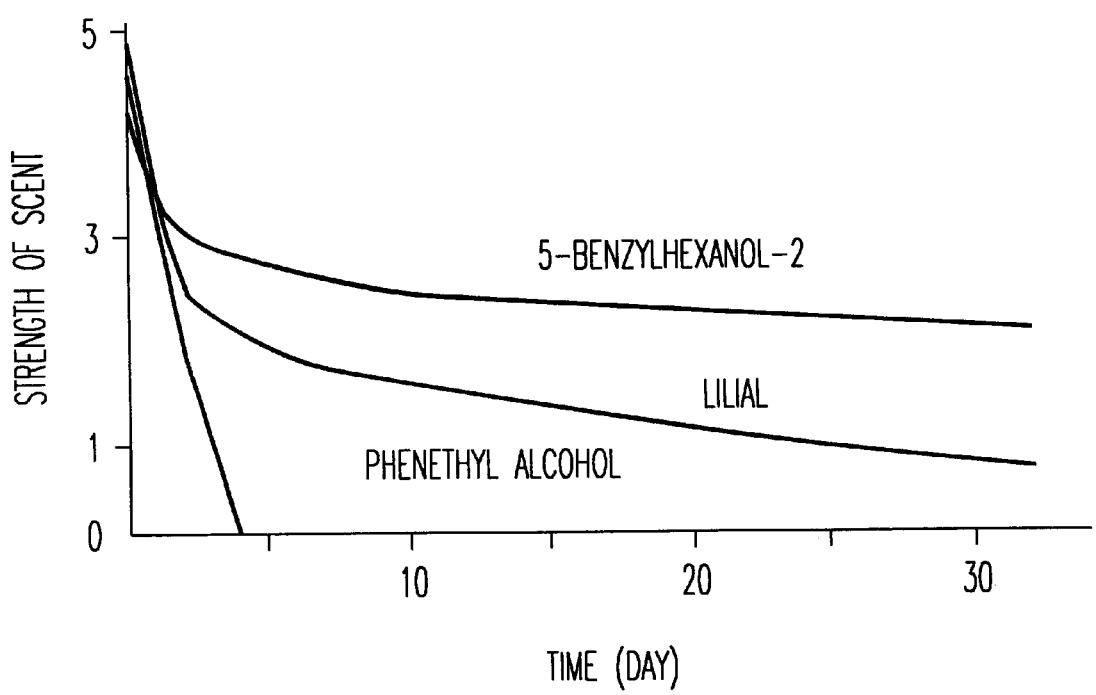
FIG. 1 illustrates the results of comparison in a scent lasting property between 5-benzylhexanol-2 and Lilial or phenethyl alcohol.

5-Benzylhexanol-2 has optical isomers based on two asymmetric carbon atoms. Any one of the isomers is embraced in the present invention.

5-Benzylhexanol-2 of the present invention is a novel compound but can be prepared in a manner known to date. Described specifically, 5-benzylhexanol-2 is prepared, for example, according to the below-described reaction scheme by introducing a methylene group into 3-phenylpropionaldehyde, which is used as a starting material, by the Mannich reaction, followed successively by hydrogenation, aldol reaction with acetone and then hydrogenation.

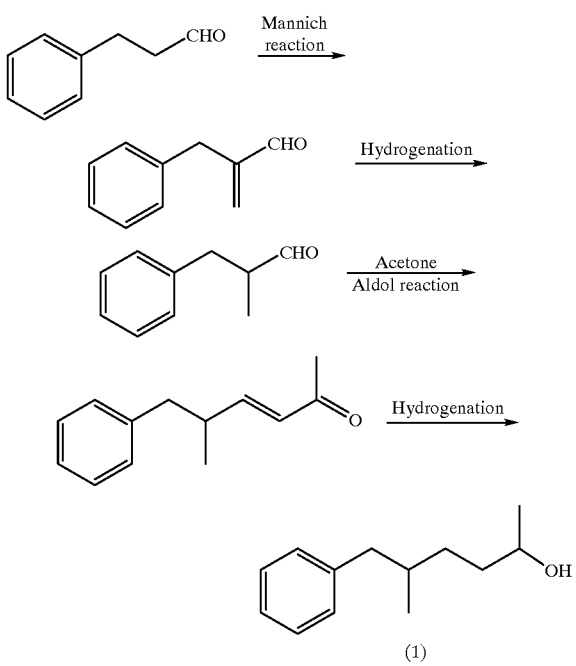

The introduction of a methylene group into 3-phenylpropionaldehyde is carried out by reacting 3-phenylpropionaldehyde with 0.8 to 1.2 times the molar weight of formaldehyde or formalin in the presence of a catalytic amount of a primary or secondary amine and a $C_{2-20}$ carboxylic acid. Examples of the primary or secondary amine include butylamine, dimethylamine, diethylamine and dibutylamine. It is preferably used in an amount of 1 to 20 mol % relative to 3-phenylpropionaldehyde. Examples of the $C_{2-20}$ carboxylic acid include acetic acid, propionic acid, butyric acid, valeric acid, hexanoic acid, heptanoic acid, octanoic acid, decanoic acid, dodecanoic acid, stearic acid, isostearic acid, cyclohexanecarboxylic acid and benzoic acid. Among them, $C_{6-16}$ fatty acids are preferred. It is preferably used in an amount of 0.1 to 20 mol % relative to 3-phenylpropionaldehyde. A reaction solvent is not always required for the above reaction, but a polar solvent such as methanol, ethanol, propanol, tetrahydrofuran or dioxane can be employed. The reaction temperature is preferably 50 to 100° C.

The resulting 2-benzylacrylaldehyde is subjected to catalytic hydrogenation in the presence of a catalyst such as palladium, in a solvent inert to the reaction such as methanol, ethanol or propanol in a hydrogen atmosphere or under pressure with hydrogen, whereby it can be introduced into 1-methyldihydrocinnamicaldehyde. As the catalyst, those supported on a carrier such as activated charcoal, zeolite, silica or alumina are preferred. The amount of the catalyst including the amount of the carrier is preferably 0.1 to 50 wt. %, particularly 0.5 to 20 wt. %, relative to 2-benzylacrylaldehyde. The reaction temperature is preferably 10 to 100° C.

The aldol reaction of 1-methyldihydrocinnamicaldehyde with acetone is effected in the presence of a base. Examples of the base include sodium hydroxide, potassium hydroxide, potassium carbonate, sodium alkoxide, potassium alkoxide and alkyl lithium. It is preferred to use the base in an amount of 0.1 to 0.7 time the molar amount of 1-methylhydrocinnamic aldehyde. It is not always necessary to use a reaction solvent, but methanol, ethanol, tetrahydrofuran or diethyl ether can be used. The reaction temperature is preferably −80 to 60° C.

The obtained 5-benzyl-3-hexen-2-one is subjected to catalytic hydrogenation in a solvent inert to the reaction, such as methanol, ethanol or propanol, in the presence of a catalyst such as Raney nickel or rhodium in a hydrogen atmosphere or under pressure with hydrogen, whereby it can be introduced into the target 5-benzylhexanol-2. The amount of the catalyst is preferably 0.1 to 50 wt. %, particularly 0.5 to 20 wt. % relative to 5-benzyl-3-hexen-2-one. The reaction temperature is preferably 10 to 100° C. After the completion of the reaction, the reaction product is purified as needed by decantation, column chromatography or the like, whereby the target 5-benzylhexanol-2 can be obtained.

5-Benzylhexanol-2 thus obtained has a floral scent and can be used as a scenting composition singly or in combination with other components.

The amount of 5-benzylhexanol-2 to be added to a perfume composition differs with the kind of other perfumes to be used in combination or the kind or strength of the target scent. Although no particular limitation is imposed on the amount insofar as the target scent can be imparted by it, it is generally preferred to add it in an amount of 0.1 to 90 wt. %, particularly 0.5 to 70 wt. %.

The perfume composition according to the present invention can be used widely for various products which need to be scented such as toiletry products, for example, perfume, soap, shampoo, rinse, detergent, cosmetics, spray and aromatic, household products and personal care products.

EXAMPLES

The present invention will hereinafter be described by examples but it should however be borne in mind that the present invention is not limited to or by them.

Synthesis Example 1

(1) 2-Benzylacrylaldehyde

A four-necked 500-ml flask equipped with a thermometer and condenser was charged with 134 g (1.0 mol) of 3-phenylpropionaldehyde, 85 g (1.05 mol) of a 37% aqueous formalin solution and 6 g (0.02 mol) of stearic acid, followed by the dropwise addition of 9 g (0.07 mol) of dibutylamine at room temperature under a nitrogen atmosphere over 10 minutes. After the temperature was increased to 90° C., stirring was conducted at the same temperature for 30 minutes. After cooling, 200 ml of water were added to the reaction mixture. The resulting mixture was then extracted with 200 ml of hexane, followed by washing with 200 ml of water. The organic layer was dried and concentrated, whereby 161 g of a crude product were obtained. The crude product was distilled (3.5 mmHg, 80° C.), whereby 110 g (yield: 75%) of 2-benzylacrylaldehyde were obtained.

$^1$H-NMR δppm: 3.57(2H,s), 6.09(2H,d,J=7.35 Hz), 7.1–7.38(5H,m), 9.62(1H,s).

(2) 1-Methyldihydrocinnamic aldehyde

In 150 ml of methanol, 104 g (0.712 mol) of 2-benzylacrylaldehyde obtained in (1) was dissolved. The resulting solution was stirred in the presence of 2 g of 5% palladium on carbon for 3 hours at room temperature under a hydrogen pressure (3 kg/cm$^2$). The reaction mixture was filtered and concentrated, whereby 98 g of 1-methyldihydrocinnamicaldehyde were obtained as a crude product.

(3) 5-Benzyl-3-hexen-2-one

In a four-necked 1-liter flask equipped with a thermometer and condenser, 7.8 g (0.2 mol) of sodium hydroxide, 25 ml of water and 360 ml of acetone were charged, followed by the dropwise addition of a solution of 97 g (0.65 mol) of 1-methyldihydrocinnamicaldehyde in 100 ml of acetone at 30° C. while stirring under a nitrogen atmosphere. After the completion of the dropwise addition, stirring was continued at room temperature for one hour. The reaction was then terminated by the addition of 12 ml (0.2 mol) of acetic acid. An excess portion of acetone was distilled off. The concentrate was dissolved in 500 ml of toluene, followed by the addition of 1.5 g of p-toluenesulfonic acid. The resulting mixture was heated and refluxed for 2 hours in a four necked 1-liter flask equipped with a thermometer, Dean Stark trap and condenser. After cooling, the reaction mixture was washed with an aqueous solution of sodium carbonate and water. The organic layer was dried and concentrated, whereby 140 g of a crude product were obtained.

In a 200-ml pear-type flask equipped with a thermometer, capillary and Claisen distillation tube, 140 g of the crude product were charged, followed by simple distillation at 0.4 mmHg. As a distillate at the top temperature of 96 to 98° C., 86 g of 5-benzyl-3-hexen-2-one (yield from 2-benzylacrylaldehyde: 65%) was obtained.

(4) 5-Benzylhexanol-2

In methanol, 10 g (53 mmol) of 5-benzyl-3-hexen-2-one obtained in (3) was stirred in the presence of 1 g of Raney nickel at room temperature under a hydrogen pressure (3 kg/cm) until the absorption of hydrogen stopped. The organic layer was fractionated by decantation, followed by concentration. The concentrate was purified by column chromatography, whereby 9.2 g (yield: 90%) of 5-benzylhexanol-2 were obtained.

$^1$H-NMR δppm: 0.86(3H,d,J=6.65 Hz), 1.17(3H,d,J=6.15 Hz), 1.7–1.8(6H,m), 2.3–2.45(1H,d), 2.57–2.75(1H,dd), 3.65–3.85(1H,m), 7.1–7.35(5H,m).

The scent of 5-benzylhexanol-2 so obtained was floral with lactone-like sweetness and it had an excellent lasting property.

Test 1: Test on scent lasting property

The scent lasting property of 5-benzylhexanol-2 of the present invention was compared with that of Lilial or phenethyl alcohol.

The test was carried out through organoleptic evaluation by a panel of 3 experts. After the tip of a 5-mm wide smelling strip was scented with each sample (50 μl), it was allowed to stand in a room. The scent lasting property was evaluated with the passage of time. The strength of the scent just after the strip was scented with Lilial was designated as 5. Based on the strength, the scent of each of other two samples was evaluated. Incidentally, strength of the scent just after a smelling strip was scented with phenethyl alcohol was 4.5, while that of 5-benzylhexanol-2 was 4.3. The results are shown in FIG. 1.

EXAMPLE 1

Orange-type fragrance

|  | (parts by weight) |
|---|---|
| Orange oil | 80 |
| Hexyl butyrate | 10 |
| Cis-3-hexenyl acetate | 10 |
| Linalol | 150 |
| Benzyl acetate | 100 |
| o-tert-Butylcyclohexenyl acetate | 100 |
| Hexyl cinnamicaldehyde | 200 |
| γ-decalactone | 50 |
| Pearlide | 100 |
| Total | 800 |

To 800 parts by weight of the above fragrance, 200 parts by weight of 5-benzylhexanol-2 were added, whereby a fruit-type fragrance with mildness, sweetness and voluminous feeling which reminded us of an apricot was obtained.

EXAMPLE 2

Jasmine type fragrance

|  | (parts by weight) |
|---|---|
| Benzyl acetate | 250 |
| Phenetyl alcohol | 200 |
| Cinnamic alcohol | 50 |
| Hydroxycitronellal | 200 |
| α-Ionone | 50 |
| Ylang-ylang oil | 48 |
| p-Cresol | 2 |
| Total | 800 |

To 800 parts by weight of the above fragrance, 200 parts by weight of 5-benzylhexanol-2 were added, whereby a jasmine type fragrance with mildness, sweetness and voluminous and spreading feeling was obtained.

CAPABILITY OF EXPLOITATION IN INDUSTRY

5-Benzylhexanol-2 has a floral scent and has, in the mixture system of a product, freshness, natural feeling, mildness, voluminous feeling and stable scent lasting property. It can be used widely for the products which require scenting such as perfume, soap, shampoo, rinse, detergent, cosmetics, spray or aromatic.

What is claimed is:

1. 5-Benzylhexanol-2 represented by the following formula (1):

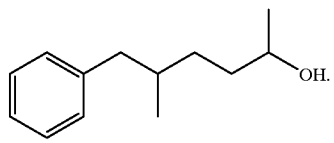

(1)

2. A perfume composition comprising 5-benzylhexanol-2.

3. A toiletry product comprising the perfume composition according to claim 2 and a toiletry product acceptable carrier.

4. A household product composition the perfume composition according to claim 2 and a household product acceptable carrier.

5. A personal care product comprising the perfume composition according to claim 2 and a personal care product acceptable carrier.

6. The toiletry product according to claim 3, wherein said toiletry product is a soap, shampoo or rinse.

7. The personal care product according to claim 5, wherein said personal care product is a perfume or a cosmetic.

8. The household product according to claim 4, wherein said household product is a detergent.

* * * * *